(12) United States Patent
Stauffer

(10) Patent No.: US 7,999,138 B2
(45) Date of Patent: Aug. 16, 2011

(54) METHYL AMINES TO OLEFINS

(76) Inventor: John E. Stauffer, Greenwich, CT (US)

( * ) Notice: Subject to any disclaimer, the term of this patent is extended or adjusted under 35 U.S.C. 154(b) by 0 days.

(21) Appl. No.: 12/691,126

(22) Filed: Jan. 21, 2010

(65) Prior Publication Data

US 2011/0178341 A1 Jul. 21, 2011

(51) Int. Cl.
*C07C 209/16* (2006.01)
*C07C 1/32* (2006.01)

(52) U.S. Cl. ......... 564/478; 564/479; 564/480; 585/638

(58) Field of Classification Search ............... 568/638
See application file for complete search history.

(56) References Cited

U.S. PATENT DOCUMENTS 2,355,314 A * 8/1944 McCorkle ............... 585/638
4,591,430 A * 5/1986 Hudson ............... 208/254 H

OTHER PUBLICATIONS

Meadows et al., J. Physical Chemistry (1961), 65, p. 2139-2143.*
Taylor, J. Physical Chemistry (1932), 36, 1960-1966.*
Taylor, J. Physical Chemistry (1930), 34, p. 2761-2770.*
Travers, Trans. Faraday Soc. (1937), 33, 1342-1353.*
Jolley, J. Chem. Soc. (1934), p. 1957-1966.*
Emeleus et al., J. Chem. Soc. (1935), p. 929-935.*
The Thermal Decomposition of Trimethylamine, Ph. D. dissertation of R. Kaufman, Catholic Univ. of Am., Washington, DC, (1963), p. 1-51 (Univ. Microfilms order No. 63-258).*
Carter et al., Journal of the Chemical Society (1939), p. 495-506.*
Travers et al., Journal of the Chemical Society (1939), p. 1360-1364.*

* cited by examiner

*Primary Examiner* — Brian J Davis
(74) *Attorney, Agent, or Firm* — Young Basile Hanlon & MacFarlane PC

(57) ABSTRACT

A process is disclosed for the production of olefins including ethylene, propylene, and butanes from methyl amine. The process comprises a reaction whereby methyl amine produces the olefin and ammonia by pyrolysis. The reaction is carried out in the gas phase at a temperature in the range of 400° C. to 700° C.

6 Claims, 1 Drawing Sheet

METHYL AMINES TO OLEFINS

SUMMARY OF THE INVENTION

The present invention relates to a process for manufacturing olefins, including ethylene, propylene, and butenes, starting with methyl amine. In the process, methyl amine, either monomethyl amine, dimethyl amine or trimethyl amine, is pyrolized to produce an olefin and ammonia. The resulting ammonia can be reused to generate mere methyl amine.

BACKGROUND OF THE INVENTION

New technology has been reported for the synthesis of olefins from methanol. (*Chemical Engineering*, January 1996, p. 17.) As described in the literature, this process converts methanol in a fluidized-bed reactor at a pressure between 1 and 5 atmospheres and a temperature in the range of 350° C. to 500° C. A zeolite-type catalyst consisting of silicon-aluminum-phosphorous oxide is used to promote the reaction.

The process is capable of converting at best about 80 percent of the methanol to ethylene and propylene in varying proportions of these olefins. With methanol selling as a premium over hydrocarbon feed-stocks, the relatively low yield of products is a drawback. Furthermore, the process is disadvantaged by the fact that heterogeneous catalysts generally undergo deactivation during usage.

Therefore, it is an object of the present invention to offer an improved method for the manufacture of olefins. This object, as well as other features and advantages, will be apparent from the following description and the figure that is included.

Other applications of the present invention will become apparent to those skilled in the art when the following description of the best mode contemplated for practicing the invention is read in conjunction with the accompanying drawings.

SUMMARY OF THE DISCLOSURE

A process is provided for the synthesis of olefins, namely, ethylene, propylene, butenes, and higher alkenes, from methyl amine including monomethyl amine, dimethyl amine, and trimethyl amine. Conversion is achieved by pyrolysis whereby the amine is heated in the gas phase to an elevated temperature so that the reactant is condensed to the olefin by splitting out ammonia The reaction may be carried out in a wide range of temperatures, preferably between about 400° C. and the 700° C. Under these conditions a series of free radical reactions occur. Relatively low pressures are required, in the range of approximately 1 atmosphere to 5 atmospheres. The retention time is critical to the success of the process. This variable is sensitive to the reaction temperature, such that higher temperatures favor shorter holding times.

A tubular reactor is well suited to the process, which is operated in a continuous manner. A furnace will maintain the reactor at the desired temperature. Effluent from the reactor is quenched before recovering the product.

Other configurations of the process will become apparent to those skilled in the art when the following description of the best mode is contemplated.

BRIEF SUMMARY OF THE DRAWINGS

The description herein makes reference to the accompanying drawings wherein like reference numerals refer to like parts throughout the several views and wherein.

DETAILED DESCRIPTION OF THE PROCESS

Figure 1:
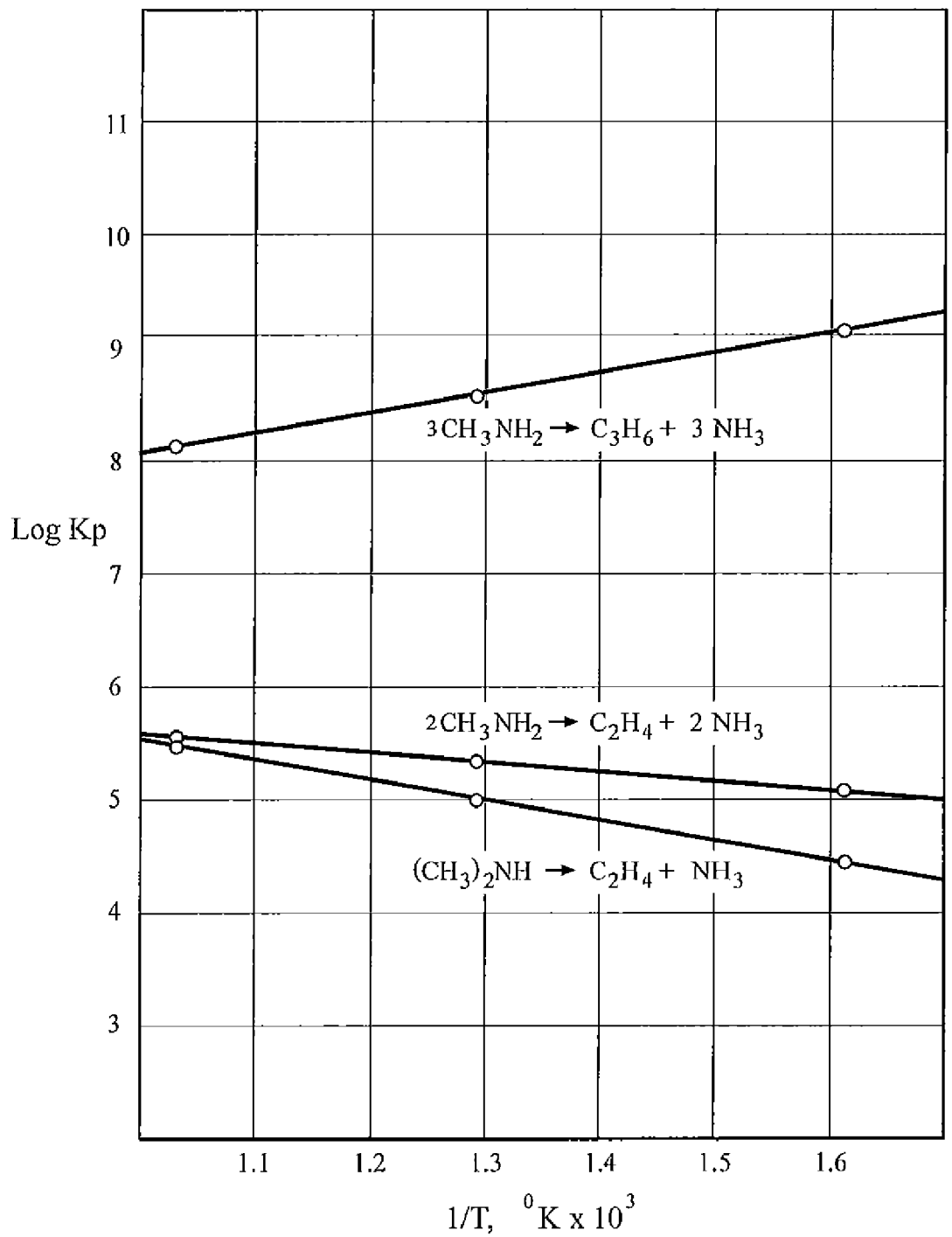
FIG. 1 is graph showing the equilibrium conversion at given temperatures for three reactions: monomethyl amine to ethylene and ammonia, monomethyl amine to propylene and ammonia, and dimethyl amine to ethylene and ammonia.

The process of the present invention comprises several chemical reactions whereby monomethyl amine $CH_3NH_2$, methyl amine $(CH_3)_2NH$, and trimethyl amine $(CH_3)_3N$ are condensed to form an olefin plus ammonia $NH_3$. The olefins may include ethylene $C_2H_4$, propylene $C_3H_4$ and butene $C_4H_8$. In addition, some higher olefins will inevitably be formed. By adjusting the reaction conditions, the ratios of the various olefins can be shifted within broad ranges.

Representative reactions of the process are shown by the following equations.

$$2CH_3NH_2 \rightarrow C_2H_4 + 2NH_3 \quad (1)$$

$$3CH_3NH_2 \rightarrow C_3H_6 + 3NH_3 \quad (2)$$

$$(CH_3)_2NH \rightarrow C_2H_4 + NH_3 \quad (3)$$

This group of reactions is not meant to be complete. For example, monomethyl amine can also form butene, and trimethyl amine can form ethylene. Which reactions take place will depend in part on the raw materials used.

Although pure monomethyl amine may be the reactant, more likely a mixture of methyl amines will be employed. Methyl amines are commonly produced by the reaction of methanol with ammonia. This process produces a mix of all three amines with boiling points that are close to each other. Because separation of the amines by distillation is relatively difficult, there is an advantage to using a crude mixture of amines in the process of the present invention.

The conversion of methyl amine to olefins is highly favorable over a wide range of temperatures. Thermodynamic data are shown in FIG. 1. Thus, for the conversion of monomethyl amine to ethylene and ammonia, the logarithm of the equilibrium constant $K_p$ equals 5.04 at 350° C. and 5.52 at 700° C.

Thermodynamic calculations also indicate that the formation of ethylene from monomethyl amine is endothermic, whereas the formation of propylene is exothermic. Thus, to a considerable extent, the heats of reaction balance each other, thereby simplifying the control of the temperature. It may, however, be necessary to supply heat to the reactor to bring the feed up to the operating temperature and to maintain it at this level.

The process of the present invention is conducted in the gas phase under pyrolysis conditions such that methyl amine condenses by means of a set of free radical reactions. For the formation of ethylene from monomethyl amine, the postulated mechanism is shown by the following equations.

$$CH_3NH_2 \rightarrow CH_3 \cdot + NH_2 \cdot \quad (4)$$

$$CH_3NH_2 + CH_3 \cdot \rightarrow C_2H_5NH_2 + H \cdot \quad (5)$$

$$CH_3NH_2 + H \cdot \rightarrow CH_3 \cdot + NH_3 \quad (6)$$

$$C_2H_5NH_2 \rightarrow C_2H_4 + NH_3 \quad (7)$$

In the above set of equations, the reaction shown by equation 4 is the initiator and will occur spontaneously at a sufficiently high temperature. In this reaction, methyl amine decomposes by homolysis to produce the two free radicals shown.

Equations 5 and 6 represent the chain reaction. They are self-propagating and occur rapidly. The ethyl amine $C_2H_5NH_2$ formed in the chain reactions decomposes to ethylene and ammonia as indicated by equation 7.

A sufficiently high temperature must be used so that the reaction kinetics are favorable. Considering the strength of the carbon-nitrogen bond, this temperature must exceed 400° C. and may be as high as 700° C. before an unacceptable quantity of byproducts is formed. The retention time plays an important role in controlling the reaction. Excessive holding times, like as is the case with too high an operating temperature, may result in unwanted soot and tar formation.

Low pressures are favored for the reaction by consideration of the stoichiometry. The moles of product exceed the moles of reactants for each of the given reactions. Nevertheless, limited pressures up to about 5 atmospheres are contemplated as a means to economize on the capital investment.

Pyrolysis is a favored method for producing olefins from methyl amine. Without sacrificing yields, high operating rates can be achieved. Not being dependent on a catalyst, the process is simple. Moreover, the process is robust and easy to install.

The present invention unavoidably generates byproduct ammonia. Therefore, some means must be found to use this material to avoid a disposal problem. The most logical approach is to use the ammonia to generate additional methyl amine from methanol, as already noted. The net result is a procedure for the manufacture of olefins from methanol, a commodity that is widely available and convenient to handle.

From the above discussion, the disclosed process for the manufacture of olefins from methyl amine can be seen to encompass a number of embodiments. Depending on circumstances, one embodiment may be preferred over another. It is the intention of the present invention to cover all such modifications and arrangements that fall within the scope of this disclosure.

The invention claimed is:

1. A process for the continuous manufacture of olefins consisting of the pyrolysis of methyl amine by heating methyl amine in the gas phase to a temperature in the range of 400° C. to 700° C. whereby an olefin and ammonia are formed by a series of free radical reactions; and further wherein the ammonia is reacted with methanol to produce additional methyl amine.

2. The process according to claim 1 in which the methyl amine is monomethyl amine.

3. The process according to claim 1 in which the methyl amine is dimethyl amine.

4. The process according to claim 1 in which the methyl amine is trimethyl amine.

5. The process according to claim 1 in which the olefin is ethylene.

6. The process according to claim 1 in which the olefin is propylene.

* * * * *